United States Patent [19]

Curtis et al.

[11] Patent Number: 5,462,915
[45] Date of Patent: Oct. 31, 1995

[54] PROCESS FOR PRODUCING MICROCAPSULES

[75] Inventors: Ralston Curtis, Mountain View; Rakesh Jain, Gilroy, both of Calif.; David C. Creech, Yuma, Ariz.; William L. Fitch, Palo Alto, Calif.

[73] Assignee: Sandoz Ltd., Basel, Switzerland

[21] Appl. No.: 201,148

[22] Filed: Feb. 24, 1994

Related U.S. Application Data

[63] Continuation of Ser. No. 907,884, Jul. 2, 1992, abandoned, which is a continuation-in-part of Ser. No. 675,847, Mar. 27, 1991, abandoned, and a continuation-in-part of Ser. No. 663,195, Feb. 21, 1991, abandoned, which is a continuation of Ser. No. 413,795, Sep. 28, 1989, abandoned.

[51] Int. Cl.$^6$ .......................... A01N 25/28; B01J 13/18; B01J 13/20
[52] U.S. Cl. .................. 504/323; 71/DIG. 1; 264/4.3; 264/4.33; 264/4.7; 428/402.21; 504/324
[58] Field of Search .................................. 264/4.3, 4.33, 264/4.7; 428/402.2, 402.21; 424/408, 462; 504/323

[56] References Cited

U.S. PATENT DOCUMENTS

| 3,074,845 | 1/1963 | Geary | 71/DIG. 1 |
|---|---|---|---|
| 3,516,941 | 6/1970 | Matson | 264/4.7 X |
| 4,105,823 | 8/1978 | Hasler et al. | 264/4.7 X |
| 4,406,816 | 9/1983 | Sliwka | 264/4.7 X |
| 4,534,783 | 8/1985 | Beestman | 264/4.7 X |
| 4,557,755 | 12/1985 | Takahashi et al. | 264/4.7 X |
| 4,956,129 | 9/1990 | Scher et al. | 264/4.7 |

FOREIGN PATENT DOCUMENTS

| 0158449 | 10/1985 | European Pat. Off. . |
|---|---|---|
| 0252897 | 1/1988 | European Pat. Off. . |
| 0350553 | 1/1990 | European Pat. Off. . |
| 2591857 | 6/1987 | France . |
| 3629714 | 3/1987 | Germany . |

*Primary Examiner*—Richard D. Lovering
*Attorney, Agent, or Firm*—Allen E. Norris; Lynn Marcus-Wyner

[57] ABSTRACT

Microcapsules formed from urea-, thiourea- and/or melamine-formaldehyde prepolymers which are particularly useful in formulating agrochemicals.

5 Claims, No Drawings

PROCESS FOR PRODUCING MICROCAPSULES

This is a continuation of application Ser. No. 07/907,884, filed Jul. 2, 1992, now abandoned, which is a continuation in part of application Ser. No. 07/675,847 filed on Mar. 27, 1991, now abandoned, and a continuation in part of application Ser. No. 07/663,195, filed on Feb. 21, 1991, now abandoned, which is a continuation of application Ser. No. 07/413,795 filed on Sep. 28, 1989, now abandoned.

The present invention concerns microcapsules formed from urea-, thiourea- and/or melamine-formaldehyde prepolymers and in particular such microcapsules containing agrochemicals.

When putting agrochemicals in a suitable form for application, formulations are desirable which optimize the effect of the active ingredient on the target organism whilst at the same time minimizing its effect on the environment, particularly with respect to animals and plants which are not targeted. One such formulation technique which in recent years has been extensively investigated with respect to agrochemicals is microencapsulation.

Examples of known microencapsulation techniques are disclosed for example in the following patents.

U.S. Pat. No. 3,516,941 describes the use of urea-formaldehyde (UF) resins for encapsulating water insoluble fill material including agrochemicals.

U.S. Pat. No. 4,105,823 describes the use of UF and melamine-formaldehyde (MF) precondensates for crosslinking with other soluble polymers to microencapsulate finely divided particulate material.

U.S. Pat. No. 4,460,722 describes a process for polycondensation of MF or UF prepolymers in the presence of a water soluble cationic urea resin and an anionic surfactant and removal of excess formaldehyde. Agrochemicals are mentioned as potentially encapsulatable substances.

U.S. Pat. No. 4,534,783 describes a discontinuous two-phase microencapsulation procedure for water soluble materials including agrochemicals.

U.S. Pat. No. 4,557,755 describes microencapsulation of agrochemicals employing a cationic urea resin forming polycondensates with UF, MF or thiourea-formaldehyde (TUF) prepolymers.

U.S. Pat. No. 4,601,863 describes the formation of microcapsules from i.a. MF prepolymers which are themselves then further treated with an aldehyde resin precondensate which is then itself polycondensed.

Each of these references in turn describes further microencapsulation techniques.

A particular problem encountered with certain agrochemicals especially herbicides when applied to the soil is their tendency to leach rapidly from the target zone when subjected to rainfall or irrigation particularly in lighter soils which include coarse to moderately coarse texture soils and soils of low organic matter content, e.g. <2.0 weight % organic matter. This problem usually precludes or restricts the use of such agrochemicals for preemergent application. Thus in the case of a herbicide suffering from this drawback, persistence in the soil zone where germination of early weeds occurs can only be achieved, if at all, by repeated application or application at higher rates which increases the risk of damage to young crop plants or is uneconomical and environmentally undesirable.

In spite of the existence of many varied microencapsulation techniques in some cases for decades it has until now not been possible to provide a commercially viable microencapsulated form of such rapidly leaching agrochemicals which will achieve the four main objectives of maintaining weed control, reducing leaching below the targeted soil zone, increasing persistence in the soil, particularly the weed seed germination zone, and preventing crop injury.

It has now surprisingly been found that excellent results can be obtained by microencapsulating a rapidly leaching agrochemical in a crosslinked polymer formed from urea-, thiourea- and/or melamine-formaldehyde prepolymers. The present invention therefore provides a process for microencapsulating a rapidly leaching agrochemical comprising the steps of a) adding to a suspension of the agrochemical in a liquid a urea-, thiourea- or melamine-formaldehyde prepolymer or mixture thereof and b) curing said prepolymer to provide a crosslinked polymer enclosing the agrochemical.

Step a) can be performed by e.g. adding to a suspension of the agrochemical in crystalline form a urea-, thiourea- or melamine-formaldehyde prepolymer or mixtures thereof.

This microencapsulation can be carried out in a single stage or in successive stages by repeating steps a) and b).

Microencapsulation according to the invention is particularly suited for agrochemicals where the usual locus of the pests or undesired plant growth to be combatted is in the upper layers of the soil. Microcapsules according to the invention can also be used in watery loci such as mosquito breeding areas or paddy fields.

Microencapsulation according to the invention is especially suited to agrochemicals where rapid leaching ability would normally preclude or restrict pre-emergent long lasting application. Examples of such agrochemicals are those containing a carboxylic acid group. Preferred examples of such compounds are herbicides particularly pre-emergent herbicides such as benzoic acid and phenoxycarboxylic acid derivatives e.g. dicamba, MCPA, 2,4-D as well as other herbicides such as alachlor, acetochlor, metolachlor and 2-chloro-N-[1-methyl-2-methoxy]-N-(2,4-dimethyl-thien-3-yl)acetamide, which is described in U.S. Pat. No. 4,666, 502.

The agrochemical may be in a solid crystalline or amorphous form or in a liquid form, e.g. an oil. The agrochemical can be soluble in the liquid in which it is suspended, but in these cases, the agrochemical must be present in excess amount, i.e. the liquid should be super-saturated with agrochemical.

This application is especially directed, therefore, to salt forms of the aforementioned herbicides which are only sparingly soluble in the liquid, e.g. water, in which they are suspended, e.g. inorganic salts such as sodium, potassium, calcium, copper, iron, aluminum or organic salts such as dimethylamine, diglycolamine, aminopropylmorpholine, and the fatty amine organic salts having carbon chains of fourteen or more atoms such as the triamylamine, tridecylamine, dimethyldodecylamine, Adogen® (primary, n-alkyl, $C_{16}$ ave.) and Primene® (primary tert-alkyl, $C_{14}$ ave.) salt forms. As suitable salt forms the sodium, potassium, calcium, iron, aluminum, dimethylamine, triamylamine or aminopropylmorpholine salts may be mentioned. Preferred salt forms are those which are only sparingly water soluble and are stable under hydrolyric conditions, e.g. the aluminum, iron, copper and calcium salts.

The aluminum and iron, i.e. the Al(III) and Fe(III) salt forms of dicamba, MCPA and 2,4-D are the preferred salt forms. It is believed that the aluminum salt of MCPA and the Fe(III) salt of MCPA and dicamba are novel.

Such salt forms can be prepared according to conventional and known procedures for preparing aluminum or iron salts of compounds that bear a carboxylic acid group, e.g. by combining the compound with a desired metal e.g. $FeCl_3$ or $AlCl_3$ in solution. In some situations, metal complexes of the compounds will be formed.

This application is also especially directed to herbicides which are only sparingly soluble in water, e.g. alachlor, acetochlor, metolachlor and 2-chloro-N-[1-methyl-2-methoxy]-N-(2,4-dimethyl-thien-3-yl)acetamide.

Suitable liquids for suspending the agrochemical are inert and are typically selected such that the agrochemical is only sparingly soluble therein. Typically, the liquid will be water, although organic liquids that are inert and in Which the prepolymer or prepolymer mix is miscible are also envisaged.

Urea-, thiourea, and melamine-formaldehyde resins, prepolymers and polymers and their preparation are known in the art and are described for example in "The Organic Chemistry Synthetic High Polymers", Robert W. Lenz, Interscience Publishers (1967) pp. 142–151; KIRK-OTHMER Encyclopedia of Chemical Technology, 3rd ed. v. 2 pp. 440–469. Many such resins are prepolymers and are also commercially available.

Particularly preferred in the practice of the invention are urea- or melamine-formaldehyde resins and prepolymers or mixtures thereof that are miscible in the liquid in which the agrochemical is suspended, with melamine-formaldehyde resins and prepolymers being especially preferred optionally mixed with urea-formaldehyde prepolymers. Where mixtures of melamine-formaldehyde (MF) prepolymers and urea-formaldehyde prepolymers (UF) are employed, the weight ratio of MF:UF preferably ranges from 1:4 to 4:1.

In order to optimize the amount of material incorporated in the microcapsules it may be desirable to have the agrochemical in sparingly soluble form e.g. preferably in a form that is less than 2% by weight soluble in the liquid in which it is suspended, more preferably less than 1% by weight soluble. In the case of agrochemicals capable of forming salts with bases for example crystalline salts with heavier metals such as aluminum or iron are preferred.

To further increase the amount of crystalline material available for encapsulation and especially in situations where wet milling of the material to a desired particle size is required prior to microencapsulation it is advantageous to reduce the amount of liquid (preferably water) used to suspend the material in most cases to form a slurry.

The desired particle size of the material to be encapsulated will vary according to the nature of the material, its intended use and prepolymer employed. As a rule satisfactory results are obtained with crystal particle sizes from 1 to 20µ, preferably 1 to 5, more preferably 2 or 3, especially ca. 2µ.

The desired particle size and active ingredient content of the finished microcapsules will also depend on intended applications. Satisfactory results are obtained with microcapsules of between 1 and 120µ, especially 10 to 50µ particularly 10 to 25µ having active ingredient content of 10 to 60% a.i. eg 30 to 60% especially 25 to 35% or 40 to 60% for use in crops. Considerably lower a.i. content of e.g. 1 to 2.5% may also be employed for example where use in home gardens or lawns is envisaged or where the active ingredient is highly active at low concentrations. In general a relatively high percentage loading of a.i. is particularly advantageous.

The desired particle size can be achieved by milling of finished agglomerated microencapsulate product or preferably by controlled crosslinking by employing multi-step addition/curing of prepolymers.

In carrying out the process according to the invention the material to be encapsulated is suspended or slurried in a liquid e.g. a solvent preferably water. It is a property of rapidly leaching agrochemicals that they exhibit relatively high solubility in water. Thus when practicing the process of the invention it is desirable to have the agrochemical in a form which is of reduced solubility in order to provide an optimal amount of material e.g. crystalline material available for microencapsulation. More soluble salt forms may be also used but are subject to stricter control of solvent amount or repeated recycling to obtain a higher percent content of a.i. if desired.

In order to avoid premature crosslinking of prepolymer it may be necessary for the suspension of a.i. to be encapsulated to be not too strongly acid at the initiation of polymerization, e.g. to have a pH of >4, especially >5.0. This can be achieved by basifying the suspension with a base however this is less desirable as it may increase solubility of the crystals. Advantageously the desired pH is achieved by having the a.i. in a crystalline form which upon suspension in the desired solvent results in the pH desired, e.g. in the form of the aluminum or iron salt.

The suspension may optionally contain further additives such as dispersants, surfactants, antifoaming agents, etc., e.g. those based on naphthalene sulphonates or acetylenic diols.

When pre-milling of the crystalline a.i. to a desired particle size is desired the suspension is preferably in the form of a slurry which may be wet-milled, e.g. by pebble milling.

Advantageously the UF/TUF/MF resins or mixtures thereof are employed in the form of prepolymers. This has the advantage of allowing elimination of undesirable traces of unpolymerized urea, thiourea, melamine and formaldehyde prior to use in the microencapsulation process.

The prepolymer or prepolymer mix is preferably added in the same liquid (e.g. solvent) used to form the slurry and is miscible in such liquid, usually water. By miscible is meant that the prepolymer or prepolymer mix is capable of mixing or dissolving in the liquid such that it surrounds the suspended agrochemical when polymerization is initiated. Addition of the desired amount of prepolymer can be carried out in one aliquot or in a series of lesser aliquots with curing after each addition. This latter procedure facilitates careful control of the particle size of the finished microcapsules and is preferred.

Alternatively, prepolymer can be formed in situ according to known methods e.g. as referenced above, and the active ingredient then added.

The ratio of prepolymer to active ingredient will vary according to the nature of the a.i. and the prepolymers themselves as well as the desired properties of the finished product. For some applications of finished products, satisfactory results are obtained with an excess of prepolymer e.g. a 1.5 to 6 fold, preferably 2 to 5 fold, especially 2 to 4 fold. For other applications of finished product, satisfactory results are obtained with an equivalent to excess amount of active ingredient, e.g. a weight ratio of prepolymer to active ingredient of 1:1 to 1:3 e.g. 1:1 to 1:2. Thus, the weight ratio of prepolymer to active ingredient employed to prepare a finished product suitably varies from 6:1 to 1:3 e.g. 2:1 to 1:3. Moreover, for some applications, the finished product may consist of a mixture of microcapsules having various prepolymer to active ingredient weight ratios.

In cases where dicamba is employed as a.i., it is preferably employed in iron or aluminum salt form. Melamine-formaldehyde and urea-formaldehyde are preferred prepolymers and are preferably employed in a weight ratio of prepolymer to dicamba salt of 4:1 to 1:2, more preferably 2:1 to 1:1.

Curing of the prepolymer or prepolymer mix can be accomplished in conventional manner, e.g. by warming or acid catalysis or both. Preferably curing is carried out by lowering pH with an acid, preferably a mild acid such as citric acid or fumaric acid to a pH below about 6, e.g. pH about 3–6, depending on the particular prepolymer and reaction conditions and warming to ca 35° to 50° C. for 2 to 10 hours or warming to 70° C. for 2 hours or longer, in each case with optional additional stirring at room temperature for ca. 24 hours. Preferably, the pH is about 5 at the initiation of polymerization and can subsequently be lowered to, e.g. 3.

Microencapsulation may be accomplished in a single stage or in repeated stages, e.g. two, three, four or more stages depending on the desired release rate of agrochemical and/or particle size. Each successive stage is carried out by repeating the steps mentioned above, i.e. by adding a quantity of prepolymer to the reaction mixture and curing by warming or acid catalyst or both.

The microcapsules may be isolated from the reaction mixture in conventional manner e.g. by filtration and/or drying.

It has also been found that under certain storage circumstances further crosslinking of the prepolymer may occur in the microcapsules according to the invention which may reduce the release rate of active ingredient contained in the microcapsule or otherwise affect the ability of the microcapsule to release the substance encapsulated therein. This lack of reliability and stability over time may under certain circumstances prove to be a serious drawback for such microcapsules.

Since discovery of this problem it has been determined that the same problem had remained generally unrecognized in the area of UF, MF and TUF polymers.

It has now surprisingly been found that this previously unrecognized problem may be solved by subjecting microcapsules formed by crosslinking a UF, MF or TUF prepolymer or mixtures thereof at conventional temperatures of 90° C. or less for example as described above to a subsequent heat-curing phase at a temperature of >100° C.

Heat curing in this manner enables microcapsules to be obtained in which the release rate remains unchanged on storage at normal conditions for up to 3 years and at accelerated storage conditions of 54° C. for up to 4 weeks. This further process according to the invention shall hereinafter be referred to as heat-curing.

The actual temperature employed will depend on various factors such as the degree of crosslinking desired, the stability of the polymer material and the material encapsulated therein, the desired profile of release of active ingredient and various others factors. The degree of acceleration of crosslinking increases with heat and it has been found that temperatures of for example 150° to 220° especially 180° to 200° are preferred for most microcapsules according to the invention especially those containing rapidly leaching agrochemicals such as e.g. dicamba and its salts.

Whilst increasing the long-term stability, heat-curing may reduce the initial release rate of the encapsulated material. In order to compensate for this effect it may be desirable to decrease the ratio of polymer to encapsulated material. It has for example been found that MF microcapsules which have been heat-cured at 200° C. and contain a ratio of polymer to encapsulated material, in this case a rapidly leaching agrochemical, of 1:2 compare favorably with the release characteristics of normally cured microcapsules having a ratio of 2:1. As will be evident this phenomenon also has clear economic advantages in enabling the additional cost which is contributed by the polymer to each unit of active ingredient to be reduced.

Further advantages of this reduced polymer to encapsulated material ratio is that smaller microcapsules are produced allowing for a reduction in dispersant required to prevent flocculation prior to initial curing and less need for reduction of particle size in the material to be encapsulated. By controlled use of dispersants a certain degree of aggregation of the smaller microcapsule may be attained to accurately control release rates. Finally, where careful control of particle size necessitated multiple curing steps in formation of microcapsules the reduction of polymer ratio enabled by heat-curing according to the invention may permit a comparable result to be obtained with fewer initial curing steps.

In a further aspect therefore the invention concerns a process for producing microcapsules by a) adding to a suspension of a substance to be microencapsulated in a liquid a urea-, thiourea- or melamine-formaldehyde prepolymer or mixtures thereof, and b) curing said prepolymer to provide a crosslinked polymer enclosing the substance to be microencapsulated wherein the microcapsules thus obtained are subsequently heat cured at a temperature of >100° C.

In a further aspect the invention concerns microcapsules prepared from crosslinked UF, TUF or MF prepolymers or mixtures thereof which exhibit substantially unchanged release characteristics of encapsulated material following storage for 4 weeks at 54° C.

When employing accelerated crosslinking caused by heat-curing according to the present invention an equivalent to excess amount of active ingredient, for example, a weight ratio of prepolymer to active ingredient of 1:1 to 1:3, eg. 1:2 or 2:3 is preferred. Thus, the weight ratio of prepolymer to active ingredient employed to prepare a finished product suitably varies from e.g. 2:1 to 1:3.

When a heat curing step according to the invention is desired the microcapsules are first isolated from the reaction mixture following the initial curing phase e.g. by filtration and then heat-cured according to the invention. Filtration followed by single-step spray-drying and heat-curing may also be mentioned.

Heat-curing according to the invention is carried out by submitting the microcapsules obtained following the initial curing to temperatures of from 100° to 250°, preferably 150° to 220°, especially about 200° for brief periods of from ½ to 3, preferably ½ to 2, especially about 1 hour. The amount of time required for heat-curing according to the invention will as a rule be inversely dependent upon the temperature, for example one hour's curing at 200° C. produces a satisfactory result for MF-capsules containing the aluminum salt of dicamba.

To facilitate application the microcapsules of the invention may be formulated in conventional manner, e.g. as dusts, granules, solutions, emulsions, wettable powders or flowables, suspensions and the like with conventional carriers and optionally other adjuvants. To prevent premature release of a.i. solid formulations are preferred. Such formulated microcapsules may be prepared in conventional manner e.g. by mixing, spray-drying and the like.

Application of the microcapsules of the present invention is made according to conventional procedure to the weeds or pests or their locus using an effective equivalent amount of active ingredient.

In the case of commercially available products, the effective amount will be based on the a.i. content and release profile of the microcapsules to correspond to the known effective application rate e.g. in the case of dicamba 0.05 to 2 lb/ac (approximately 0.055 to 2.2 kg/ha), especially 0.1 to 1 lb/ac (approximately 0.11 to 1.1 kg/ha). The optimum usage of the microcapsules of the present invention is readily ascertainable by one of ordinary skill in the art using routine testing such as greenhouse testing and small plot testing.

For example, in the pre-emergent control of weeds a half-life of from 7 to 60 days, e.g. 30 to 45 days, preferably 40 to 60 days would be desirable (time required for 50% of a.i. to be released from the microcapsule.)

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight equivalent of active ingredient. Lower or higher levels of active ingredient can, of course, be present depending on the intended use, the physical properties of the microcapsules and the mode of application. Concentrate forms of a composition intended to be diluted before use generally contain between 2 and 90%, preferably between 5 and 81% by weight equivalent of active ingredient.

Agriculturally acceptable additives may be employed in the composition to improve performance and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms e.g. water or diesel oil.

In another aspect the invention therefore concerns an agriculture composition comprising a rapidly leaching agrochemical microencapsulated in a crosslinked urea-, thiourea- or melamine-formaldehyde prepolymer or mixed prepolymer according to the present invention together with an agriculturally acceptable carrier.

A further aspect of the invention therefore concerns a method of controlling undesirable pests or plant growth which comprises applying to the locus or anticipated locus of said undesirable pests or plant growth an effective amount of a rapidly leaching agrochemical microencapsulated in a crosslinked urea-, thiourea- or melamine-formaldehyde prepolymer or mixed prepolymer according to the present invention.

Microcapsule formulations may optionally contain further active ingredient such as herbicide, insecticides, acaricides, fungicides and the like. For example, it may be advantageous to formulate the same or other active ingredients in unencapsulated form to achieve initial control prior to the onset of controlled release from the microcapsules. Such unencapsulated material can for example be applied in the form of a spray dried coating on the microcapsules. Alternatively, premix or tank-mix of unencapsulated with encapsulated material can be appropriate.

Combinations of unencapsulated and encapsulated material should be formulated in amounts and applied at rates sufficient to achieve initial weed control without causing undue crop damage. In the case of dicamba, satisfactory results are achieved when the unencapsulated form is applied at a rate ranging from about 0.125 to 0.25 lb/ac (about 0.138 to 0.28 kg/ha) whilst the encapsulated form is applied at a rate of about 1.0 lb a.i./ac (about 1.1 kg a.i./ha). Thus, suitable weight ratios for formulations containing unencapsulated and encapsulated dicamba range from 1:8 to 1:4 unencapsulated:encapsulated a.i.

As a further alternative a formulation may consist of a mixture of microcapsules having various prepolymer to a.i. weight ratios.

Combinations mentioned above can allow for effective, continuous control over periods as long as 1 to 75 days.

The following examples illustrate the invention. Temperatures are given in degrees centigrade.

EXAMPLE 1 a) Preparation of the Aluminum Salt of Dicamba 100 g of dicamba aminopropyl morpholine salt (prepared by mixing technical dicamba, aminopropyl morpholine and distilled water) in 150 ml of deionized water are mixed with 21.8 g of $AlCl_3$ $6H_2O$ in 44 ml of water at 80° for 2 hours, cooled to 40° and filtered.

b) Preparation of Microcapsules

The wet filter-cake of Example 1a (dicamba-Al content ca. 40 g) is slurried with 50 ml of deionized water and 2.0 g of Morwet D425 (Sodium Naphthalene Formaldehyde Condensate—Petrochemicals Company, Inc.) is pebble milled for 9 hrs, a further 20 ml of deionized water and 0.5 g of Morwet D425 are added and milling continued for a further 2 hrs to give a final median particle size of 3.7μ. This slurry is diluted with deionized water to 188 g. To this slurry are added with stirring 172 g of diluted urea-formaldehyde prepolymer (prepared by refluxing 24 g of urea and 48 g of formaldehyde for 1 hr at 70° with stirring and diluting the result with 100 ml of deionized water), 40 g of CYMEL® 385 Resin (methylated melamine-formaldehyde resin formulation containing approximately 80% by weight active resin, M.W. approximately 250,—American Cyanamid Company) and 2 g of citric acid dropping the pH of the slurry from 6.0 to 5.1. The temperature is slowly raised to 50° with a water bath. After stirring for 2½ hrs the pH is 4.1. After stirring for a further 4 hrs a further 1 g of citric acid is added reducing pH further to 3.2. After an additional 1½ hrs stirring, the mixture is cooled to 40°, filtered and dried at 54° to yield 77 g of median particle size 15.7μ.

EXAMPLE 1.1 a) Preparation of the Iron Salt of Dicamba 93.0 g of technical dicamba is dissolved in 250 ml water containing 52.0 g of 45% KOH. The pH is adjusted to 7.0 with extra KOH or dicamba. While the above solution is stirred a second solution consisting of 36.7 g $FeCl_3$ $6H_2O$ dissolved in 71.0 g water is added dropwise over a period of 1½ hrs. When complete the resulting slurry is warmed to 60° C. for 2 hrs. After cooling the salt is filtered, washed and dried at 54° C.

b) Preparation of Microcapsules 25.0 g of the salt from part a) is transferred to a (000) Norton pebble mill along with 4.0 g of Morwet D425, 2 drops of Surfynol® TG-E (acetylenic diol surfactant—Air Products and Chemicals Inc.) and water to make a total of 100 g. This slurry is milled for 10 hrs reducing the mean particle size to 2.2μ.

The above milled salt is transferred to an 800 ml beaker and while mixing with an overhead mounted stirrer, 16.6 g of Cymel® 385 is added along with 2 drops of Foamaster® FLM (30% silicone emulsion defoamer— Henkel Corp.) and citric acid to pH 5.6. The system is warmed by water bath to 50° C. for 30 min and cooled to 25° C. During the warming cycle a 4.4% solution of Morwet D425 in water is added to thin the solution and maintain proper mixing. This procedure is repeated twice, each time using 16.6 g of Cymel® 385. The total volume is doubled after the last addition of Morwet solution. The capsule slurry is stirred for 24 hours total, filtered, washed and dried at 54° C. to yield capsules containing 18.8% a.i. with a mean particle size of 21μ.

EXAMPLE 2 a) Preparation of Aluminum Salt of Dicamba 110.5 g of technical dicamba acid are added with stirring to a mixture of 62.35 g of 45% aq KOH and 95.65 g of deionized water. A mixture of 60.355 g of $AlCl_3$ $6H_2O$ in 125 g of deionized water is then added with stirring over a 5 minute period followed by further 10 g of deionized water. A further 31.16 g of 45% aq KOH and 10.33 g of deionized water are then added and the resulting mixture refluxed for 2 hrs with stirring at 80° C. The resulting mixture is then filtered.

b) Preparation of Microcapsules

A slurry of the wet filter cake from Example 2a) (Dicamba-Al content ca. 30 g) is pebble milled with 115 g of deionized water 4 g of MORWET D425 and 3 drops of SURFYNYL® TG-E to a median particle size of 1.8μ. To this slurry is added 20 g of CYMEL 385 in 40 g of deionized water and 1 g of citric acid to pH 5.4 and the temperature raised (water bath) over a 2 hr period to ca. 40°. After cooling to ca 25° a further 20 g of CYMEL 385 in 50 g of deionized water are added and the temperature again raised to ca 40° over 1 hr. This procedure is repeated with a further 20 g of CYMEL 385 in 44 g o deionized water. After final cooling the mixture is filtered and the microcapsules dried at 54° to yield a median particle size 18.9μ.

EXAMPLE 3

The procedure is analogous to Example 2 except that the higher temperature in the microencapsulated phase is 50° rather than 40°. Microcapsules of median particle size 20.3μ are obtained.

EXAMPLE 4 a) Preparation of Aluminum Salt 600 g of dicamba, 98 g of NaOH and 800 ml of water are stirred together for 1 hr to dissolve the solids (temperature rise to 60°).

Separately 328.2 g of aluminum chloride hexahydrate are dissolved with stirring in 600 ml of water and 88 g of conc. ammonium-hydroxide added slowly over 5 minutes to precipitate aluminum hydroxide which redissolves in 1 hr (pH 2.5).

This solution is then added slowly over 1 hr to the dicambate solution with vigorous stirring and following completion of the reaction, stirring is continued for 1 hr (final pH ca 3).

The aluminum dicambate is then removed by filtration and either directly used further or dried for storage.

b) Preparation of Microcapsules (polymer:dicamba ratio 2:3)

A subsample of the wet cake previously obtained above containing 275 g of the aluminum dicambate is charged to a (0) size pebble mill along with the equivalent of 450 g of water, 9.1 g Morwet® D425 (A)* and 5 drops of Surfynol® TGE (B)*. Approx. 320, ½×½ inch ceramic cylinders are used as grinding media. The mill is run 5 hrs reducing the median particle size to 2.2–2.6μ with about 5% 8–12μ.

The milled slurry is diluted with water to a total of 1900 g, 180 g of Cymel® 385 (C)* added with stirring and the pH adjusted, if necessary, to 5.0–5.2 with citric acid. The mixture is stirred at 50° C. for 45 min. Foaming is controlled by dropwise additions of Foamaster® FLM (D)*. Stirring is continued an additional 24 hours at R.T.

The resulting capsules are recovered by filtering, washed with about 1600 mls of water and dried at 54° to yield capsules with a median diameter of 12–20μ containing 50% active ingredient.

c) Formulation of Microcapsules and Heat Curing

The dried capsules can be formulated as a wettable powder by adding a preground mixture of 10 g of Igepon® T-77 (Sodium-B-methyl-N-Oleoyl Taurate; Rhone-Poulenc) and 10 g of Morwet® D425 and chain whipping to uniformity.

Alternately, the slurry may be spray dried directly to a wettable powder after adding the surfactants to a suitably diluted suspension.

Following its preparation the wettable powder is placed in open dishes and heated for one hour at 200° C.

*Legend:
[A=Sodium Naphthalene Formaldehyde Condensate—Petrochemicals Co. Inc. B=Acetylenic diol surfactant—Air Products & Chemicals Inc. C=Methylated melamine formaldehyde resin—American Cyanamid Co. D=Silicone based antifoamant—Henkel Corp.]

EXAMPLE 5

The active ingredient content of the microcapsules is determined by heating the capsules with concentrated HCl, diluting the resultant solution, and analyzing by HPLC with external standard quantitation.

The a.i. content of the capsules of Examples 1, 1.1, 2, 3 and 4 is 33, 18.8, 33, 31 and 50% respectively.

EXAMPLE 6

Formulation as wettable powder

The following components are combined to yield a wettable powder.

a) Microcapsules according to Example 2b): 94%
b) Aerosol OTB (American Cyanamid—Diotylester of Na-Sulfosuccinic acid): 3% and c) Morwet D425: 3%

The inerts are preground before mixing with microcapsules to avoid capsule breakage.

EXAMPLE 6.1

Sprayable Formulation

75 Parts by weight of microcapsules prepared according to Examples 1, 1.1, 2 or 3 are slurried in water. 25 Parts of Morwet D425 are added and the resulting mixture is spray dried to yield a sprayable formulation.

EXAMPLE 7

Evaluation of leaching characteristics

Glass leaching columns, 5-cm long and 9-cm diameter, are packed with soil to achieve a bulk density of approximately 1.4 g/cm$^3$, which is similar to that in a field. The soil consists of 72.1% sand, and 16.9% silt and 11.0% clay. The organic matter content is 0.9% and the pH is 8.1.

The columns packed with soil are first saturated with water by allowing about 400 mls of deionized water to leach through them. Excess water is allowed to drain out of the columns by leaving them undisturbed overnight. The soil surface in each column is then sprayed with 5-ml solutions of the formulations containing 2.5 mg a.e. (corresponding to a 4 kg a.e./ha) using an atomizer. Treated columns are then leached with 85, 170, or 510 mls of water corresponding to 0.5, 1.0, or 3.0 inches rainfall equivalent. The flow rate of water is adjusted to approximately 1 ml/min. The leachate from each column is collected and analyzed by UV absorbance using HPLC.

| Results | Amount of dicamba released (mg) | | | % release of total applied |
|---|---|---|---|---|
| | 1st irrigation | 2nd irrigation | 3rd irrigation | |
| 0.5 inch | | | | |
| A | 0.4 | 2.0 | 0.2 | 100 |
| B | 0.0 | 1.9 | 0.3 | 88 |
| 1.0 inch | | | | |
| A | 2.1 | 0.1 | 0.0 | 88 |
| B | 0.1 | 1.9 | 0.1 | 84 |
| 3.0 inch | | | | |
| A | 2.1 | 0.0 | 0.0 | 84 |
| B | 0.4 | 1.5 | 0.1 | 80 |

A = BANVEL ® (Aqueous solution of dicamba-DMA)
B = Microcapsules according to Example 4

EXAMPLE 8

Field Test

Velvetleaf, red root pigweed and morningglory seeds are planted and tilled ca. 2 inches (5.1 cm) deep and corn seed then sown. The microcapsules of Examples 1, 2 and 3 (as wettable powders) and Banvel® (dimethylamine salt of Dicamba—Sandoz Crop Protection Corporation) are then applied to the soil surface by spraying aqueous tank mix at a rate of 1 lb per acre (about 1.1 kg/ha dicamba acid equivalent) with 3 replications. One inch (2.54 cm) of water is applied immediately after application followed by 1.25 inches (3.2 cm) 2 days later. Weed control and corn injury are evaluated 2 weeks after treatment. After evaluation a further 3 inches (7.6 cm) of water are applied over a 2 day period. Plots are treated with Gramoxone Super (paraquat, ICI Americas Inc.) at 0.5 lb a.i. per acre (about 0.55 kg/ha) and 5 days later velvetleaf and pigweed are resown and further 2.5 inches (6.4 cm) of water applied. Evaluation of weed control takes place 42 days after replanting.

The formulations of Examples 1, 2 and 3 showed no control at two weeks compared with BANVEL whereas after 65 days control was as follows:

| Examples | % of Control Velvetleaf | Pigweed |
|---|---|---|
| 1 | 81 | 84 |
| 2 | 85 | 84 |
| 3 | 96 | 98 |
| Banvel | 0 | 0 |

Additionally the formulations of Example 1, 2 and 3 caused little if any corn injury whereas Banvel caused significant injury.

This demonstrates the excellent persistence in the weed target zone of the microcapsules according to the invention compared with the same active ingredient in conventional form and their safety as regards crop injury.

What is claimed is:

1. A process for producing microcapsules by
   a) adding to a suspension of a substance to be microencapsulated in a liquid a urea-, thiourea- or melamine-formaldehyde prepolymer or mixtures thereof, and
   b) curing said prepolymer to provide a crosslinked polymer enclosing the substance to be microencapsulated wherein the improvement comprises heat-curing the microcapsules thus obtained at a temperature of >100° C.

2. A process according to claim 1 wherein the heat-curing takes place at a temperature of 150°–220° C.

3. A process according to claim 1 wherein the substance to be encapsulated is a rapidly leaching agrochemical.

4. A process according to claim 1 wherein the ratio of prepolymer to active ingredient is from 1:1 to 1:3.

5. A process according to claim 1 wherein the agrochemical is dicamba, 2,4-D or MCPA.

* * * * *